United States Patent [19]

Siegel et al.

[11] 4,272,635
[45] Jun. 9, 1981

[54] PRODUCTION OF ALKALI METAL PHENATES

[75] Inventors: Sanford A. Siegel; Masao Yoshimine; Che-I Kao, all of Midland, Mich.

[73] Assignee: The Dow Chemical Company, Midland, Mich.

[21] Appl. No.: 60,945

[22] Filed: Jul. 26, 1979

[51] Int. Cl.³ .................. C07C 39/24; C07C 39/36
[52] U.S. Cl. ................................ 568/776; 568/777
[58] Field of Search ............. 568/776, 774, 778, 777

[56] References Cited

U.S. PATENT DOCUMENTS

| | | | |
|---|---|---|---|
| 1,036,087 | 8/1912 | Flemming | 568/774 |
| 1,991,329 | 2/1935 | Mills | 568/776 |
| 2,769,833 | 11/1956 | Weil | 568/774 |
| 2,843,635 | 7/1958 | Pennington | 568/776 |
| 3,055,950 | 9/1962 | Fike et al. | 568/778 |

FOREIGN PATENT DOCUMENTS

| | | | |
|---|---|---|---|
| 722210 | 11/1965 | Canada | 568/776 |
| 718779 | 11/1954 | United Kingdom | 568/776 |

*Primary Examiner*—Werren B. Lone
*Attorney, Agent, or Firm*—Joyce P. Hill; Douglas N. Deline

[57] ABSTRACT

A molten substituted phenol and an aqueous caustic solution are reacted at temperatures from 170° C. to 190° C. under superatmospheric pressure to form an aqueous solution of an alkali metal phenate. By employing a rapid drying process such as flashing the water vapor from the reactor to cool the mixture, alkali metal phenate solids are produced with low levels of toxic by-products.

10 Claims, No Drawings

PRODUCTION OF ALKALI METAL PHENATES

BACKGROUND OF THE INVENTION

Alkali metal compounds of substituted phenols are usually prepared by reacting the substituted phenol with the appropriate base. The substituted phenols react with strong bases to form salts called phenates.

Referring particularly to the preparation of sodium pentachlorophenate as an illustration, it is known to prepare this material by reacting molten pentachlorophenol at about 90° C. with sodium hydroxide in water to form a solution having about 35 weight percent sodium pentachlorophenate based on the total weight of the aqueous reaction product. This solution is subsequently dried in a fluid bed dryer at high temperatures (200° C.-280° C.) and long residence times (average 4 hours) to yield the product in bead form. The conditions of drying promote the formation of toxic by-products which are undesirable in the product mix. Illustrated below are the undesirable reactions and by-products that occur during the drying conditions.

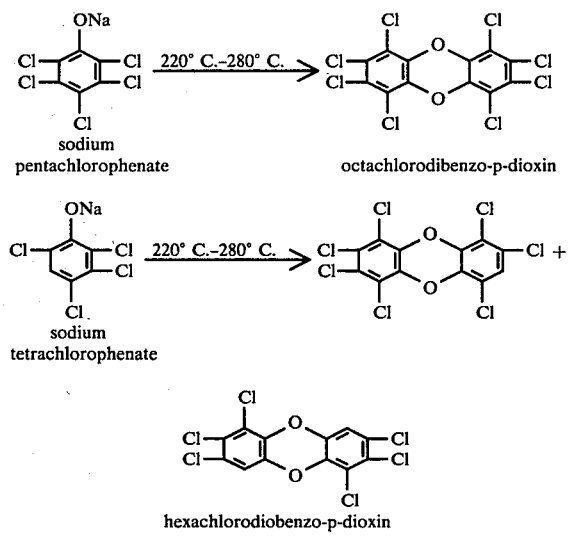

To date, present commercial practices for the preparation of sodium pentachlorophenate require that the reaction occur in the presence of water or a liquid reaction medium which must subsequently be removed. Dioxin formation is integrally associated with the heat history of the drying process. For use as an antimicrobial agent, it is also desirable and usually specified that the sodium pentachlorophenate contain not more than, and preferably less than, 1 ppm hexachlorodibenzo-p-dioxin and 30 ppm octachlorodibenzo-p-dioxin. Present facilities using a fluid bed dryer cannot routinely produce alkali metal phenates which meet desired dioxin specifications.

Industrial interest in economic production techniques and environmentally-safe products, fosters a continuing effort to frugally produce an antimicrobial substance, having the activity and water-solubility of an alkali metal phenate, such as sodium pentachlorophenate, without the toxic by-products.

In accordance with the present invention, an alkali metal phenate is obtained in an energy saving process and with little or no dioxin formation.

SUMMARY OF THE INVENTION

In a sealed, pressurized reaction vessel, substantially pure, molten substituted phenol is reacted with an aqueous solution of a caustic alkali at temperatures from 170° C. to 190° C. to form an aqueous solution rich in alkali metal phenate. Subsequent rapid drying, such as, flashing of the water vapor from the reactor cools the reaction mixture and produces a solid alkali metal phenate having safe, no-effect levels of toxic by-products.

DETAILED DESCRIPTION OF THE INVENTION

In the appropriate environment, the instant reaction may be illustrated as follows:

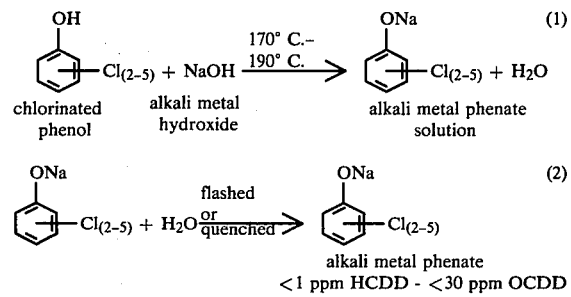

This is only one embodiment of the invention, of course.

As used herein, the term "substituted phenol" means that the phenol ring structure has at least one substituent in addition to the —OH radical; the additional substituent being selected from the group consisting of halogen, phenyl, alkyl of up to 22 carbon atoms, and alkoxy of up to 22 carbon atoms. Suitable such substituted phenols include mono-, di-, tri-, tetra- and pentachlorophenol; mono-, di-, tri-, tetra- and pentabromophenol, and the various isomeric forms; ortho-, meta- and para-phenylphenol; 2-, 3-, 4-ethoxyphenol; 2-, 3-, 4-methoxyphenol; 2-, 3-, 4-propoxyphenol; 2-, 3-, 4-butoxyphenol; 2-, 3-, 4-methylphenol; 2-, 3-, 4-ethylphenol; 2-, 3-, 4-propylphenol; 3,4,5,6-tetrabromo-o-cresol; 2,4,5,6-tetrabromo-m-cresol; 2,3,5,6-tetrabromo-p-cresol; 3,4,5,6-tetrachloro-o-cresol, 2,4,5,6-tetrachloro-m-cresol; 2,3,5,6-tetrachloro-p-cresol, and the like. Pentachlorophenol is especially preferred at present.

The alkali metal hydroxides useful in this reaction are hydroxides of sodium, potassium, cesium, niobium, lithium, rubidium, and francium. For economic reasons sodium hydroxide is preferred.

In the present invention, the alkali metal hydroxide is employed in the form of an aqueous solution to facilitate the reaction between the alkali metal hydroxide and molten substituted phenol. The amount of water used in preparing the aqueous caustic solution is calculated after determining the percent of anhydrous alkali-metal phenate desired in the final reaction product. However, because one mole of water is generated for each mole of alkali-metal phenate formed, the amount of water added is adjusted accordingly. Below is a formula which may be used to determine the total amount of water required for the production of 1 mole of an end-product having 65 percent sodium pentachlorophenate (NaP) and 35 percent water ($H_2O$):

$$Y[A(Z/(100-Z)-B] = X$$

wherein Y is the number of moles of NaP, A is the molecular weight of 1 mole of NaP, Z is the percent of H$_2$O in the final aqueous solution, B is the molecular weight of 1 mole of H$_2$O and X is the weight of H$_2$O required to form the desired aqueous reaction product. Solving for X, in the specific example above, $$1[288.29(35/(100-35))-18]=X,$$

X = 137.23 grams of water

Thus, 137.23 grams of water are required for the production of 1 mole of NaP when the desired final product contains 65 percent NaP and 35 percent H$_2$O. The calculated amount of water, less the amount of water generated by the reaction, is then used to form an aqueous caustic solution prior to contact with the molten pentachlorophenol reactant. In a similar manner, the starting amount of water is computed for the manufacture of products having varying concentrations of the alkali-metal salt and water in the product. It is preferred that the aqueous caustic solution have 25 to 50 percent sodium hydroxide based on the total weight of the caustic solution.

The solubility of an alkali-metal phenate in water is also a consideration in determining operating temperatures and conditions. An aqueous alkali-metal phenate solution remains uniform in a temperature region bordered by the observed melting point and freezing point of the aqueous alkali-metal phenate solution. Although other conditions, such as, agitation and super-cooling, can alter solubility of the phenate in water; the degree of solubility based on temperature provides adequate data for the process of this invention. It is also most efficient to operate this process in the temperature range where the substituted phenol is in a molten or liquid phase. Optimum operating conditions are achieved when a specific temperature range is found wherein the aqueous alkali-metal phenate product and the molten substituted phenol remain fluid. As an example, the following data on the solubility of sodium pentachlorophenate in water indicate specific temperature ranges within which uniform aqueous sodium pentachlorophenate solutions are formed.

| Weight Percent Anhydrous Sodium Pentachlorophenate | Solution Point °C. | Freezing Point °C. |
|---|---|---|
| 50.08 | 129 | * |
| 57.53 | 140 | 123–124 |
| 60.59 | 145 | 129–131 |
| 63.76 | 152 | 131–133 |
| 75.58 | 200 | 174 |
| 81.50 | >200 | * |
| 85.00 | >200 | * |

*Not of interest because the operating temperatures would not be in a range where sodium pentachlorophenate is in a molten state (i.e., 175° C.-310° C.).

The above data also indicate that the aqueous sodium pentachlorophenate reaction product would remain a uniform solution at temperatures from about 125° C. to about 200° C. and contain from about 50–80 weight percent sodium pentachlorophenate based on the total weight of the aqueous product solution. However, using a temperature range suitable for handling molten pentachlorophenol, the solubility data suggests that optimum operating parameters are expected when the sodium pentachlorophenate product contains from about 65–75 percent NaP and 25–35 percent H$_2$O.

The instant alkali-metal hydroxide-substituted phenol reaction is preferably conducted neat (i.e., without any solvent added). A molten, purified substituted phenol, such as pentachlorophenol containing less than 1 ppm HCDD and less than 30 ppm OCDD, is reacted with an aqueous solution of a caustic alkali at temperatures between 165° C. and 200° C., preferably between 170° C. and 190° C. with vigorous stirring for short intervals of from 0.05 to 30 minutes, preferably from 3 to 12 minutes under superatmospheric pressure of from 15 to 500 pounds per square inch gauge (psig), preferably from 90 to 250 psig. A 30 to 85 percent alkali-metal phenate solution is formed in the heated autoclave. Heat is turned off and the pressure of the reactor is released. The heat of the reaction is sufficient to flash off the steam which comprises 15 to 70 percent of the alkali-metal phenate solution. The reactor is sufficiently cooled by flashing off the water in the system without the addition of cooling water. The reactor is then cooled to room temperature and samples of the reaction product are analyzed for HCDD and OCDD using liquid chromatography.

As an alternative to flashing off the steam at the end of the reaction, any suitable means may be used to rapidly dry the alkali metal phenate so as to avoid prolonged exposure to high temperatures (e.g., above 200° C.) as in processes using the fluid bed dryer. For example, unbound moisture in the reaction product may be removed by methods which permit short contact time with heat, such as, spray drying, pneumatic conveyor drying, vacuum drying and the like. However, the currently preferred drying method comprises flashing off the water vapor formed during the reaction, thereby cooling and isolating a solid alkali metal phenate having substantially no toxic by-products. Unnecessary handling and manipulating of the aqueous reaction product mixture is also avoided.

The following examples illustrate the invention but are not to be taken as limiting its scope. In the examples, quantities of material are expressed in terms of parts by weight, unless otherwise specified.

EXAMPLE 1

In a one liter, nickel reactor equipped with a 500 milliliter (ml) stainless steel loading cylinder, a pressure release system, temperature controller, heating, and cooling jacket is placed 266 parts (1 mole) of purified pentachlorophenol. The reactor is then sealed. To the 500 ml loading cylinder is added 128 parts of a caustic solution having 35.5 percent sodium hydroxide (1.075 mole) and 64.5 percent water. The loading cylinder is then pressured with air to 340 psig and preheated to 100° C. The reactor is then heated to 200° C. to melt the pentachlorophenol prills. After the desired temperatures for the reactor and loading cylinder are reached, the stirrer within the reactor is activated, the valve between the caustic cylinder and the reactor is opened and the hot caustic solution is forced into the reactor and mixed with the molten pentachlorophenol. The molten pentachlorophenol-caustic solution is stirred vigorously for 3 minutes while the temperature is maintained at 185° C.–186° C. and the pressure is maintained at 230 psig. After 3 minutes reaction time, the heater is turned off; cooling water is turned on to the reactor jacket and the pressure of the reactor is released. After 7 minutes of cooling, whitish solids are recovered and are analyzed to reveal 83 percent ±3 percent sodium pentachlorophenate plus 17 percent water (97 percent ±3 percent recovery). Dioxins were not detected using a liquid chromatograph, DuPont Model 840 or equivalent. Detection limits for the equipment are 0.1 ppm for HCDD and 2 ppm for OCDD.

The analytical method for detecting dioxins comprises separating the chlorinated dibenzo-p-dioxins from the alkali-metal phenate by reverse phase partition chromatography using a constant-composition mobile phase with ultraviolet detection of the column effluent. Quantitation is achieved by comparison of peak areas from the resulting chromatogram to peak areas of known standards.

EXAMPLES 2–5

Using substantially the same technique as described in Example 1, summarized in Table I below are conditions and results of the reactions of 266 parts of distilled pentachlorophenol with 23.8 percent caustic solution (43 parts NaOH and 137 parts $H_2O$) and 35.5 percent caustic solution (43 parts NaOH and 82.5 parts $H_2O$) for 65 percent and 75 percent sodium pentachlorophenate based on the total weight of the aqueous solution produced, respectively.

TABLE I

Sodium Pentachlorophenate Formation
<1 ppm HCDD and <30 ppm OCDD

| Example No. | Temperature (°C.) | Time (Minutes) | Wt. % Pentochlorophenate | HCDD ppm | OCDD ppm |
|---|---|---|---|---|---|
| *Distilled Pentachlorophenol | | | | N.D.$^3$ | 3 |
| 10$^{a,c}$ | 180 | 3 | 65 | 0.35 | N.D.$^e$ |
| 11$^{a,c}$ | 180 | 3 | 75 | N.D.$^d$ | N.D.$^e$ |
| 12$^{b,c}$ | 185 | 3 | 75 | 0.10 | 12 |
| 13$^{b,c}$ | 187 | 12 | 75 | 0.26 | 4.5 |

Yields for the above examples are 97 percent ::3 percent.
*Not a part of this invention, for comparison only.
$^a$Pressured with $N_2$.
$^b$Pressured with air.
$^c$No quench.
$^d$Not detected. Detection limits 0.1 ppm for HCDD.
$^e$Not detected. Detection limits 2 ppm for OCDD.

We claim:

1. A process for the preparation of an alkali metal phenate which comprises the steps of reacting by mixing a molten chlorinated phenol with an aqueous caustic solution in a sealed, pressurized reactor vessel, under superatmospheric pressure, at a temperature from about 165° C. to about 200° C., until the caustic solution is sufficiently reacted with the substituted phenol, cooling and isolating the solid alkali metal phenate product by rapidly drying the aqueous reaction product mixture in a manner which permits short contact time with heat.

2. The process of claim 1 wherein the substituted phenol is pentachlorophenol.

3. The process of claim 2 wherein the pentachlorophenol contains less than 1 ppm hexachlorodibenzo-p-dioxin and less than 30 ppm octachlorodibenzo-p-dioxin.

4. The process of claim 1 wherein the aqueous caustic solution comprises sodium hydroxide and water.

5. The process of claim 1 wherein the drying step is accomplished by flashing the water vapor formed during the reaction from the reactor vessel when the temperature inside the reactor is between about 150° C. and about 200° C.

6. The process of claim 1 wherein the alkali metal phenate is sodium pentachlorophenate prepared by reacting molten pentachlorophenol with about a 25 percent to a 50 percent aqueous solution of sodium hydroxide, based on the total weight of sodium hydroxide and water, at temperatures from about 170° C. to about 190° C. under superatmospheric pressure.

7. The process of claim 6 wherein the superatmospheric pressure is from about 15 to about 250 pounds per square inch gauge.

8. The process of claim 6 wherein the sodium pentachlorophenate contains from about 50 percent to about 80 percent sodium pentachlorophenate based on the total weight of the reaction product.

9. A process for minimizing toxic dioxin formation in the production of an alkali metal phenate which comprises the steps of reacting by mixing a molten chlorinated phenol with an aqueous caustic solution in a sealed, pressurized reactor vessel, under superatmospheric pressure, at a temperature from about 165° C. to about 200° C., until the caustic solution is sufficiently reacted with the substituted phenol, cooling and isolating the solid alkali metal phenate product by rapidly drying the aqueous reaction product mixture in a manner which permits short contact time with heat.

10. The process of claim 9 wherein the drying step is conducted at a temperature below 200° C.

* * * * *

UNITED STATES PATENT AND TRADEMARK OFFICE
CERTIFICATE OF CORRECTION

PATENT NO. : 4,272,635  Page 1 of 2
DATED : June 9, 1981
INVENTOR(S) : Sanford A. Siegel, Masao Yoshimine and Che-I Kao It is certified that error appears in the above—identified patent and that said Letters Patent is hereby corrected as shown below:

Column 1, line 35, that portion of the formula reading

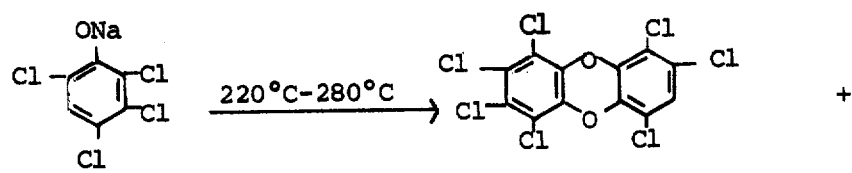

sodium tetrachlorophenate should read

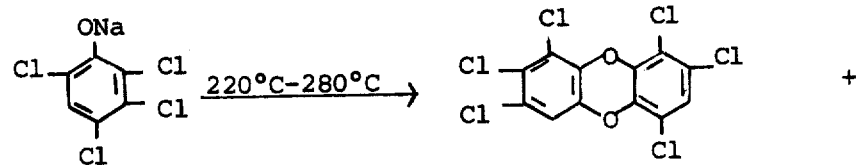

sodium tetrachlorophenate

UNITED STATES PATENT AND TRADEMARK OFFICE
CERTIFICATE OF CORRECTION

PATENT NO. : 4,272,635

DATED : June 9, 1981

INVENTOR(S) : Sanford A. Siegel, Masao Yoshimine and Che-I Kao

It is certified that error appears in the above-identified patent and that said Letters Patent is hereby corrected as shown below:

Column 5, line 28, the fourth heading in Table I "Petochlo-" should read -- Pentachlo --.

Column 5, line 30, the fifth column in Table I, "N.D.$^3$" should read -- N.D.$^e$ --.

Column 5, line 36, the first footnote of Table I, "97 percent : : 3 percent" should read -- 97 percent $\pm$ 3 percent --.

Signed and Sealed this

Twelfth Day of January 1982

[SEAL]

Attest:

GERALD J. MOSSINGHOFF

Attesting Officer

Commissioner of Patents and Trademarks